United States Patent [19]

Kurz

[11] 4,413,978
[45] Nov. 8, 1983

[54] ORTHODONTIC RETAINER

[76] Inventor: Craven H. Kurz, No. 6 North Star, Apt. 106, Marina del Rey, Calif. 90291

[21] Appl. No.: 379,051

[22] Filed: May 17, 1982

[51] Int. Cl.³ .............................................. A61C 7/00
[52] U.S. Cl. ...................................................... 433/6
[58] Field of Search ........................................ 433/5, 6

[56] References Cited

U.S. PATENT DOCUMENTS

| | | | |
|---|---|---|---|
| 3,849,885 | 11/1974 | Robins | 433/6 |
| 3,903,604 | 9/1975 | Snead | 433/5 |
| 4,253,828 | 3/1981 | Coles et al. | 433/6 |

*Primary Examiner*—Robert Peshock
*Attorney, Agent, or Firm*—Keith D. Beecher

[57] ABSTRACT

An orthodontic retainer is provided for maintaining a patient's teeth properly positioned after the teeth have been aligned by orthodontic treatment. The retainer consists of a first metallic member in the form of an arcuate band formed, for example, of silver-chromium alloy, which is configured to conform with the lingual surface of the teeth of the patient's arch, and which is cemented to the lingual side of the arch, this member serving to retain the teeth in their proper positions which were achieved through previous orthodontic treatment. The retainer also includes a transparent plastic member in the form of a second arcuate band formed, for example, of acrylic, which extends around the labial side of the arch and which conforms with the labial surfaces of the teeth. The transparent plastic member is removable, and it is held in place by elastics or other ligatures which are fitted on posts on the ends of the plastic member and on corresponding posts on the ends of the metallic member.

3 Claims, 2 Drawing Figures

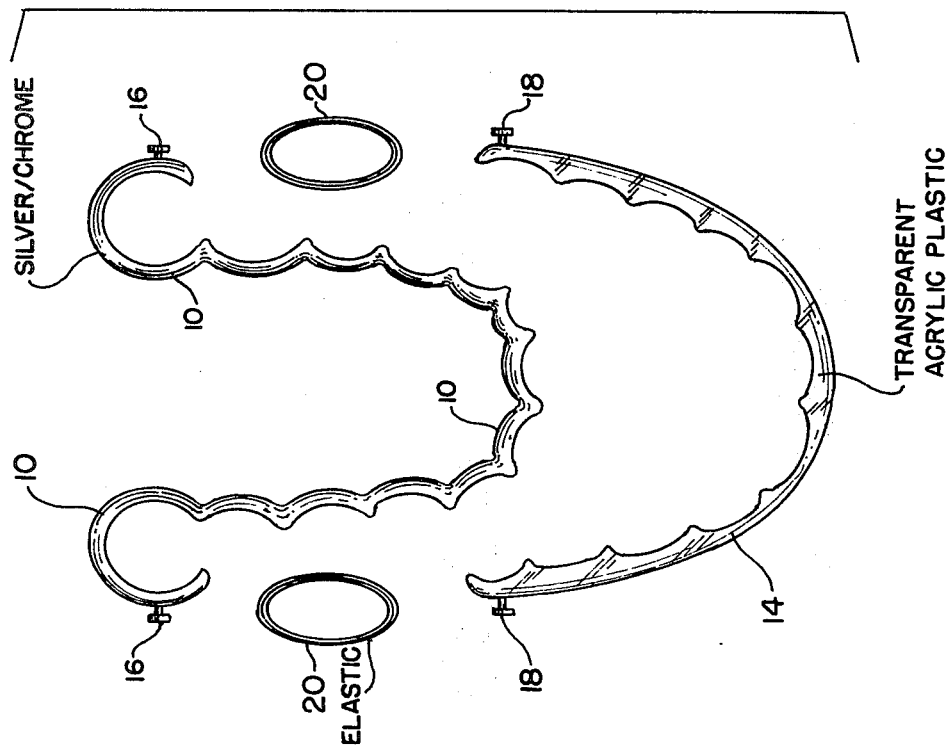
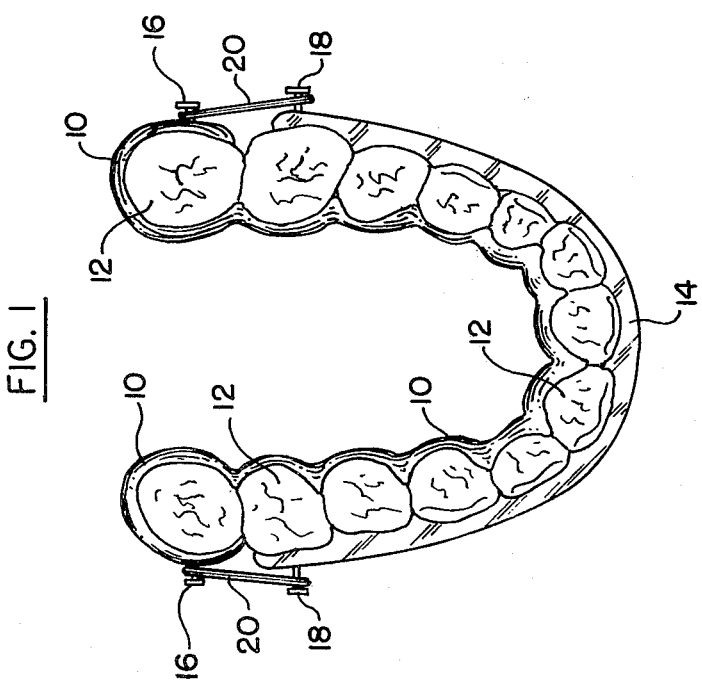

ORTHODONTIC RETAINER

BACKGROUND OF THE INVENTION

After a patient's teeth have been properly aligned by orthodontic treatment, it is the usual practice to fit a retainer into the mouth of the patient which serves to hold the teeth in their proper positions to which they have been shifted by the orthodontic treatment, and prevent the teeth from moving back to their original positions prior to the orthodontic treatment.

Such retainers are usually worn for prolonged periods. The prior art retainers for the most part are a combination of plastic and attached metal wires. They impede speech, and are often unsightly constituting a source of embarrassment for the wearer.

The retainer of the present invention is, for the most part, invisible and comfortable to wear. The labial member of the retainer is not cemented to the arch and can be removed. Because the lingual member is very thin it can be worn alone by the patient during the daytime without interferring with the patient's speech, and it also is invisible. During the evening hours, the labial portion may be attached to prevent rotations of the teeth that have been straightened.

BRIEF DESCRIPTION OF THE DRAWING

FIG. 1 is a top plan view of an arch of a patient, showing a retainer constructed in accordance with the present invention in place for retaining the teeth of the arch in their proper positions; and FIG. 2 is an exploded view showing the two members which make up the retainer of FIG. 1; and elastic ligatures for supporting the labial member in place on the arch.

DETAILED DESCRIPTION OF THE ILLUSTRATED EMBODIMENT

The retainer of the invention includes a first member in the form of an arcuate band 10 which is formed of metal, such as silver-chrome alloy. Band 10 is configured to conform with the lingual surfaces of the teeth of an arch 12. The retainer also includes a second member in the form of an arcuate band 14 which is formed, for example, of a transparent plastic material such as acrylic. The band 14 conforms with the labial surfaces of the teeth of the arch 12. The arcuate lingual band 10 is provided with a pair of posts 16 at its opposite ends; and the arcuate labial band 14 is provided with a pair of posts 18 at its opposite ends. A pair of elastic ligatures 20 extend around the posts, so as to hold the labial band 14 firmly in place.

The resulting retainer is practically invisible, because of the transparent nature of labial band 14, and because lingual band 10 is mounted on the lingual surfaces of the teeth. Also, labial band 14 can be removed by the patient, merely by removing the ligatures 12, so that the retainer continues to function by virtue of the invisible lingual band 10.

The invention provides, therefore, an improved orthodontic retainer which is comfortable to wear, and which does not produce an unsightly appearance and does not impede speech.

It will be appreciated that while a particular embodiment of the invention has been shown and described, modifications may be made, and it is intended in the claims to cover all modifications which come within the true spirit and scope of the invention.

What is claimed is:

1. A retainer assembly for use in conjunction with the teeth of an arch of a patient, said assembly comprising: a first metallic arcuate band configured to conform with the lingual surface of the teeth of the arch extending around the lingual side of the arch to be cemented to the lingual side of the arch so as to hold the teeth in particular post-orthodontic treatment positions; a second transparent removable plastic arcuate band separate from the first band and configured to conform with the labial surfaces of the teeth of the arch and extending around the labial side of the arch also serving to hold the teeth of the arch in their post-orthodontic treatment positions, posts mounted at the respective ends of each of said first and second arcuate bands; and elastic ligatures extending around respective pairs of said posts resiliently to secure said arcuate bands to one another.

2. The retainer assembly defined in claim 1, in which said first arcuate band is formed of a silver-chrome alloy.

3. The retainer assembly defined in claim 1, in which said second arcuate band is formed of a transparent acrylic plastic material.

* * * * *